(12) United States Patent
Bovio et al.

(10) Patent No.: US 11,504,274 B2
(45) Date of Patent: Nov. 22, 2022

(54) DEPTH DETECTION APPARATUS IN PARTICULAR IN INTRACORNEAL DISSECTION

(71) Applicant: EYECODE S.R.L., Milan (IT)

(72) Inventors: Dario Bovio, Galliate (IT); Caterina Salito, Milan (IT); Barbara Uva, Losanna (CH); Alfonso Iovieno, Eboli (IT); Luigi Fontana, Bologna (IT)

(73) Assignee: EYECODE S.R.L.

( * ) Notice: Subject to any disclaimer, the term of this patent is extended or adjusted under 35 U.S.C. 154(b) by 177 days.

(21) Appl. No.: 16/613,980

(22) PCT Filed: May 18, 2018

(86) PCT No.: PCT/IB2018/053512
§ 371 (c)(1),
(2) Date: Nov. 15, 2019

(87) PCT Pub. No.: WO2018/211465
PCT Pub. Date: Nov. 22, 2018

(65) Prior Publication Data
US 2021/0338483 A1 Nov. 4, 2021

(30) Foreign Application Priority Data
May 18, 2017 (IT) .......... 102017000053993

(51) Int. Cl.
*A61F 9/007* (2006.01)
(52) U.S. Cl.
CPC .............. *A61F 9/00763* (2013.01)
(58) Field of Classification Search
CPC ....... A61B 3/16; A61B 3/165; A61F 9/00736; A61F 9/00763; A61F 9/00745; A61F 9/00754; A61F 9/007; A61F 9/00781
See application file for complete search history.

(56) References Cited

U.S. PATENT DOCUMENTS

2014/0194834 A1* 7/2014 Passaglia ............ A61F 9/00781
604/290

FOREIGN PATENT DOCUMENTS

GB    867128       5/1961
WO    2017044965 A1   3/2017

OTHER PUBLICATIONS

Feizi, Sepehr, "Use of deep anterior lamellar keratoplasty (DALK) for keratoconus: indications, techniques and outcomes," Expert Review of Ophthalmology, 2016, pp. 347-359, vol. 11, No. 5.

* cited by examiner

*Primary Examiner* — Majid Jamialahmadi
(74) *Attorney, Agent, or Firm* — Laubscher & Laubscher PC

(57) ABSTRACT

A depth detection apparatus, in particular in intracorneal dissection, provides a perforating tubular element suitable for being inserted into the cornea, a reciprocally moving air volume generator (14) connected to the perforating tubular element, a pressure sensor for detecting the pressure along the connection between the volumetric generator and the perforating element in the reciprocal movement of the volumetric generator, a microcontroller connected to the pressure sensor to detect pressure variations with the depth advancement into the cornea of the perforating element, a signaller connected to the microcontroller to signal that a preset pressure variation has been reached. The apparatus enables a correct position to be determined for performing intracorneal dissection.

8 Claims, 2 Drawing Sheets

DEPTH DETECTION APPARATUS IN PARTICULAR IN INTRACORNEAL DISSECTION

CROSS REFERENCE TO RELATED APPLICATIONS

This application is a § 371 National Stage Entry of International Patent Application No. PCT/IB2018/053512 filed May 18, 2018. Application No. PCT/IB2018/053512 claims priority of IT102017000053993 filed May 18, 2017. The entire content of these application is incorporated herein by reference.

BACKGROUND OF THE INVENTION

The present invention relates to an apparatus that detects the depth in a surgical operation, in particular in a dissection surgical operation inside the cornea (intracorneal).

The cornea is the transparent window of the eye, located in a central position and in front of the iris, the crystalline lens and the retina. The cornea holds the largest portion of the refractive power of the human eye. From an anatomical point of view, the cornea divides into three layers: the surface epithelium, the intermediate stroma, and the internal endothelium. These layers are divided by two membranes, the Bowman membrane between the epithelium and stroma and the Descemet membrane between the stroma and the endothelium.

A corneal transplant, which is known as keratoplasty, consists of replacing the corneal tissue in order to obtain vision rehabilitation from corneal pathologies.

Keratoconus, a degenerative pathology of the corneal stroma, constitutes, depending on the geographical area, one of the if not the most frequent indication for corneal transplant.

For many years, the only available keratoplasty technique was penetrating keratoplasty, abbreviated as PK, where the entire thickness of the corneal tissue is replaced. The progress made over the last 20 years in corneal surgery enables us today to perform also "lamellar" keratoplasty, in which selective replacement of the diseased corneal layer ("lamella") takes place whilst the healthy parts of the cornea are saved.

Of these lamellar keratoplasty techniques, deep anterior lamellar keratoplasty, abbreviated as DALK, allows the selective excision and transplant of the corneal stroma whilst saving the endothelium of the recipient. This surgical technique has very numerous indications in the surgical treatment of corneal stromal pathologies, including, for example, keratoconus. Over the years, different techniques have been proposed to perform DALK (layer-by-layer dissection, intrastomal dissection, dissection by cleavage), conceived with the common purpose of obtaining total or subtotal removal of the corneal stroma up to the possible exposure of a descemetic or pre-descemetic plane.

The depth and uniformity of dissection are particularly important and post-operative vision results depend on them closely. In one of the most common DALK techniques, the so-called "Big Bubble" technique, the forced injection of air inside the corneal stroma allows detachment by cleavage of the deep stroma from the descemetic or pre-descemetic plane, minimizing the residual stroma amount.

The comparison between the results of PK and DALK in the vision rehabilitation of patients with corneal stroma diseases has been the subject of numerous scientific publications. Although equivalent vision results have been obtained, DALK has proved to be superior to PK in terms of survival of the transplant, risk of rejection, post-operative astigmatism and resistance to trauma. Last but not least, in view of the higher cost and execution time, DALK has proved to be also economically advantageous over the long term owing to a better cost-benefit ratio. On the basis of such scientific evidence, there is a substantial international consensus in recommending DALK as the surgical procedure to be optioned for stromal corneal disease/opacity that does not involve the endothelium layer.

Despite the unquestionable superiority and the international consensus, DALK has not been able to reach the expected level of popularity and diffusion on the global scene. Compared with PK, in fact, DALK requires more time and execution difficulty, with a steep and long learning curve that is accessible only to the operator who performs high volumes of surgery.

The element of greatest difficulty in DALK surgery is identifying a deep stromal plane that enables stromal dissection of equal depth to be performed. Currently, determining the dissection plane is widely entrusted to the experience of the surgeon. This subjective evaluation introduces an element of unpredictability into the correct execution of the DALK technique. To prove this, the reported success rate of the "Big Bubble" technique is 60-80% of the cases also in the most expert hands. In fact, it is difficult also for the expert surgeon to determine visually the correct intrastomal positioning of the injection cannula in a tissue the central thickness of which is little more than half a millimetre. Using Optical Coherence Tomography (OCT) intraoperative equipment has been shown, in recent studies, to be able to provide quantitative assistance to intrastomal dissection during DALK. However, this technology still possesses significant technical limitations and is burdened by very high costs.

OBJECT OF THE INVENTION

The object of the present invention is to propose an apparatus that enables the surgeon to determine a correct depth to perform intracorneal dissection.

BRIEF DESCRIPTION OF THE INVENTION

This object is achieved by an apparatus for detecting depth in the intracorneal dissection.

BRIEF DESCRIPTION OF THE DRAWINGS

In order to better understand the invention, a description is given below of a nonlimiting exemplary embodiment thereof, illustrated in the attached drawings in which.

DETAILED DESCRIPTION OF THE INVENTION

Figure 1:
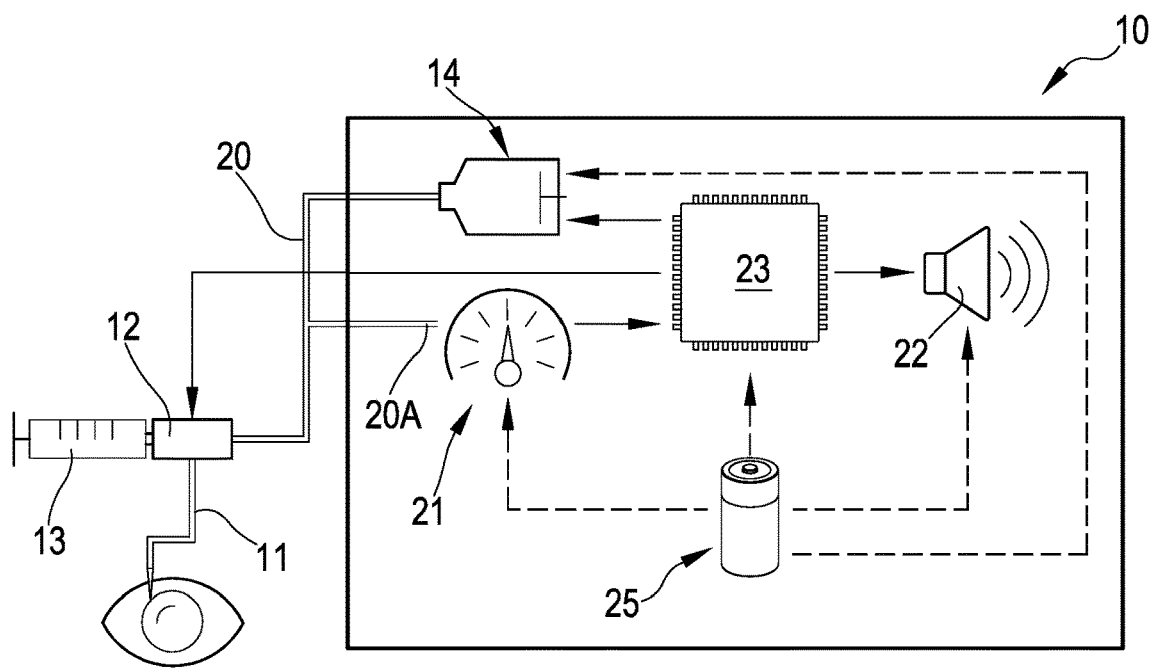
FIG. 1 is a schematic drawing of an apparatus for detecting depth in the intracorneal dissection according to the invention.
Figure 2:
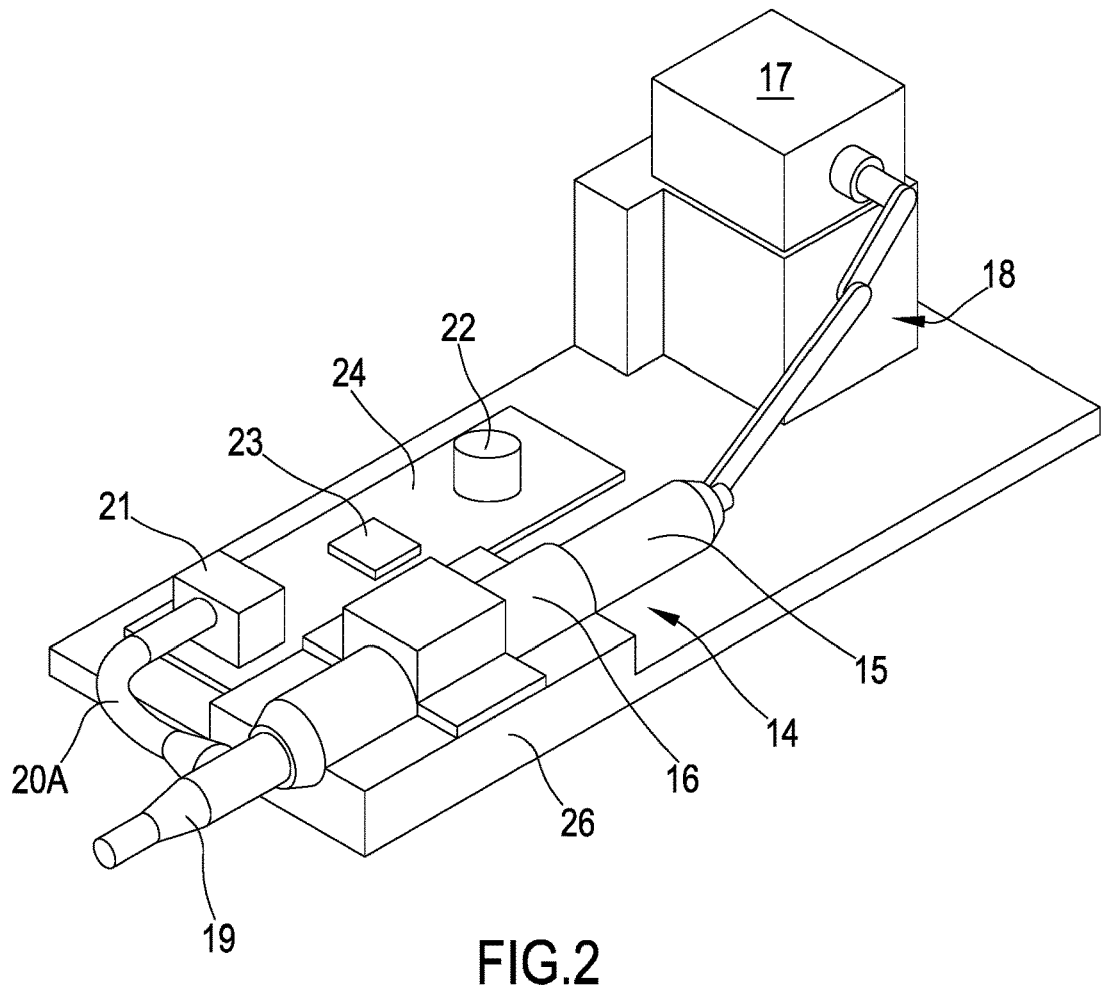
FIG. 2 is a schematic perspective view of the internal part of the apparatus of FIG. 1.
Figure 3:
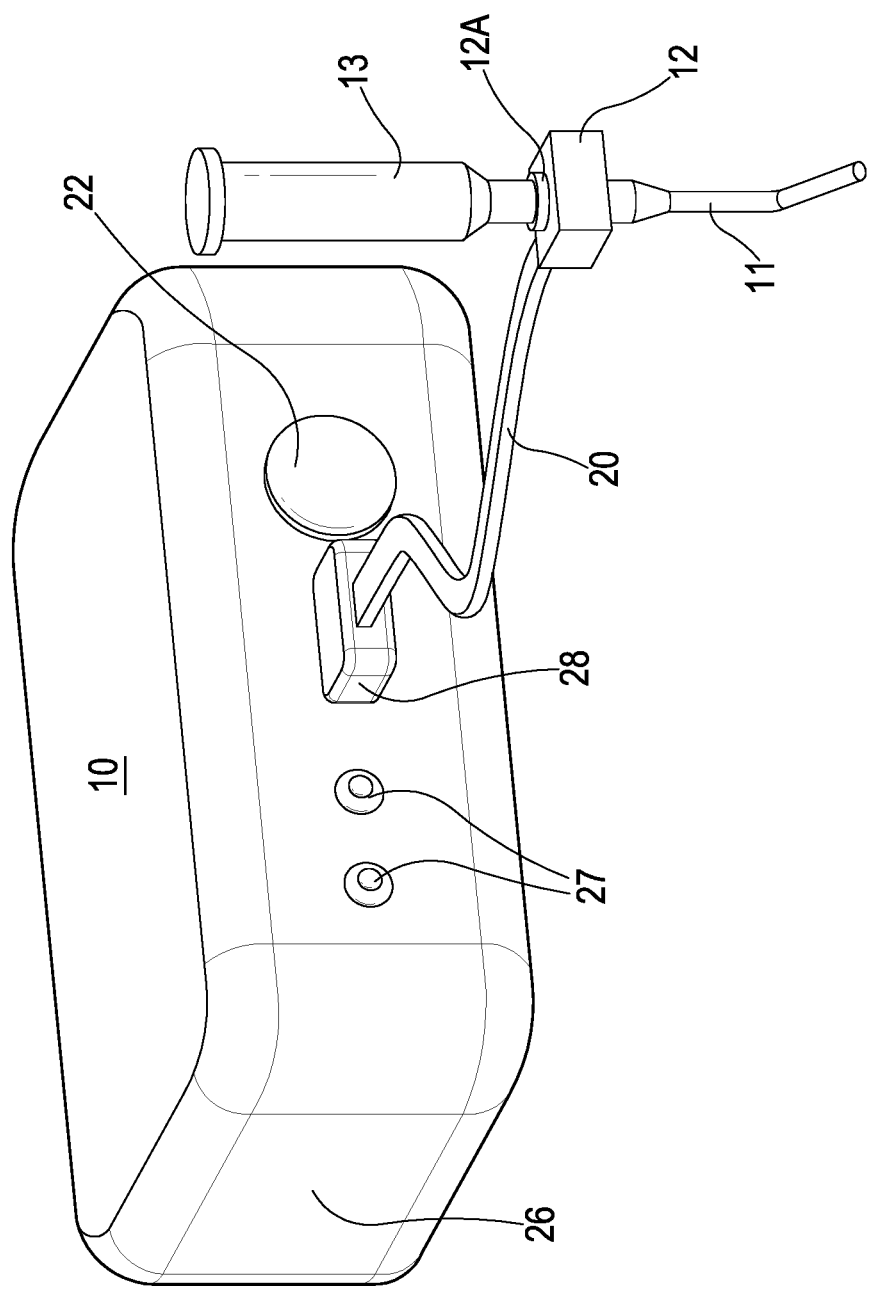
FIG. 3 is a perspective view of the external part of the apparatus of FIG. 1.

The detection apparatus illustrated, generically indicated by 10, provides a perforating tubular element for access to the eye by the operator and a series of devices associated to the perforating tubular element.

The perforating tubular element consists of a needle/cannula 11.

The needle/cannula 11 is fitted and connected to a three-way and two-position solenoid valve 12, to a connection 12A of which a syringe 13 can be connected.

As regards the devices of the apparatus 10, the following is provided.

First of all, a reciprocally moving air volume generator is provided, indicated by 14, formed by a piston 15 slidable in a cylinder 16 and by a drive that drives the piston 15 with reciprocating motion. The drive consists of a reduction gear 17 and of a connecting rod/crank cinematic mechanism 18 that connects the reduction gear 17 to the piston 15. The cylinder 16 is connected to the valve 12 through a pneumatic fitting 19 and a semi-rigid tube 20.

A pressure sensor 21 is then provided that is connected through a tube 20A to the pneumatic fitting 19 and consequently to the tube 20.

An acoustic signaller 22 and a microcontroller 23 fitted to an electronic board 24 complete the devices. The microcontroller 23 is connected to the solenoid valve 12, to the reduction gear 17, to the pressure sensor 21, and to the acoustic signaller 22.

All the devices disclosed above are supplied by a battery 25.

A casing 26 contains the devices and the battery 25. On the front of the casing 26 the acoustic signaller 22 and LED indicators 27 are visible.

The electrical connection between the microcontroller 23 and the solenoid valve 12 is incorporated into the tube 20. A connector 28 provides a removable connection between a tube 20 with an electric connection and devices inside the casing 26.

The operation of the apparatus 10 is as follows.

In the present embodiment the use of the apparatus 10 is disclosed in the case of a deep anterior lamellar keratoplasty or DALK surgical operation, described in the introductory part.

The apparatus 10 is started in such a manner that the solenoid valve 12 is in the connection position between needle/cannula 11 and generator 14, excluding the connection 12A of the syringe 13, and in such a manner that the piston 15 is set in motion owing by the reduction gear 17 with reciprocal movement owing to the crank mechanism 18. At each outward stroke in the direction of the pneumatic fitting 19 the piston 15 sends a predetermined minimal volume of air to the needle/cannula 11 through the tube 20.

At this point the surgeon slowly introduces the needle/cannula 11 into the cornea of the eye to be operated.

During delamination of the corneal stroma the pressure sensor 21 detects continuously the pressure of the air sent to the needle/cannula 11, in the stroke of the piston 15, and the pressure of the air in the small air pocket formed in the corneal tissue, and sends these data to the microcontroller 23. The microcontroller 23 is thus able to analyze continuously the pressure value given by the reciprocal volumetric stimulation as the needle/cannula penetrates the corneal stroma.

The collagen lamellae of the corneal stroma are densely packed and oriented in a front-rear direction in the front two thirds of the stroma whereas they are more loosely organized and are arranged orthogonally in the lower third, the plane where the intrastomal dissection DALK should be performed to obtain optimum cleavage. For this reason, there is a progressive reduction of the elastic resistance of the corneal stroma with the depth.

Owing to this progressive reduction of the elastic resistance, the microcontroller 23 detects a pressure difference that increases with the perforation depth.

When a depth of the corneal stroma has been reached that corresponds to an optimum dissection plane, the microcontroller 23 detects a significant variation of the pressure difference, in accordance with preset values, and commands the acoustic signaller 22 to emit a sound to alert the surgeon.

At this point, the surgeon injects forced air at this optimum depth to obtain detachment by cleavage of the stroma in accordance with the "Big Bubble" technique seen in the introduction.

In order to introduce the forced air, the surgeon can use the syringe 13 connected directly to a needle/cannula introduced into the cornea up to the previously detected optimum dissection point or can use the same needle/cannula 11 by connecting the syringe 13 to the solenoid valve 12 by switching of the solenoid valve 12 to the other position in which the connection 12A of the syringe is connected to the needle/cannula 11 and the tube 20 is excluded.

The apparatus 10 thus enables the surgeon to determine a correct position to perform intracorneal dissection.

It should be noted that this has been obtained with a simple, cheap and reliable apparatus.

Although the apparatus 10 is designed and intended specifically to assist in the surgical operation of intracorneal dissection, the use thereof cannot be excluded for other eye surgery or other types of surgery where similar needs arise.

It is clear that variations on and/or additions to what has been disclosed and illustrated above can be provided.

In particular the reciprocal volumetric generator can be of another type, even if the one disclosed and illustrated is simple and effective.

In addition to or in place of the acoustic signaller, luminous signaller can be used. In a sophisticated version, the apparatus can provide a display that shows the pattern of the pressure variation to the surgeon.

Instead of the battery supply, a mains power supply can be used.

The invention claimed is:

1. A depth detection apparatus for intracorneal dissection, comprising a perforating tubular element suitable for being inserted into a cornea, a reciprocally moving air volume generator connected to the perforating tubular element, a pressure sensor for detecting a pressure along the connection between the reciprocally moving air volume generator and the perforating element in the reciprocal movement of the reciprocally moving air volume generator, a microcontroller connected to the pressure sensor to detect variations in the pressure with the advancement in depth into the cornea of the perforating element, a signalling device connected to the microcontroller to signal that a preset pressure variation has been reached.

2. The depth detection apparatus according to claim 1, wherein along the connection between the reciprocally moving air volume generator and the perforating element there is provided a three-way valve with a connection for a syringe that is suitable for introducing forced air into the cornea for dissection, the three-way valve being switchable between a position in which the reciprocally moving air volume generator is connected to the perforating element and the connection of the syringe is disconnected from the perforating element and a position in which the reciprocally moving air volume generator is disconnected from the perforating element and the connection of the syringe is connected to the perforating element.

3. The depth detection apparatus according to claim 2, wherein the three-way valve is a solenoid valve connected to the microcontroller to be activated in one or the other of said positions.

4. The depth detection apparatus according to claim 1, wherein the reciprocally moving air volume generator is connected to the microcontroller to be activated in an operating step.

5. The depth detection apparatus according to claim 1, wherein the perforating tubular element is a needle/cannula.

6. The depth detection apparatus according to claim 1, wherein the reciprocally moving air volume generator comprises a piston that is slidable in a cylinder, driven with reciprocating motion.

7. The depth detection apparatus according to claim 6, wherein the piston is driven with reciprocating motion by a reduction gear through a connecting rod/crank cinematic mechanism.

8. The depth detection apparatus according to claim 1, wherein the signalling device comprises an acoustic signaller.

\* \* \* \* \*